US012586333B2

(12) United States Patent　　　　(10) Patent No.:　US 12,586,333 B2
　　　Kim et al.　　　　　　　　　　(45) Date of Patent:　Mar. 24, 2026

(54) AUTOMATED METHOD FOR GENERATING PROSTHESIS FROM THREE DIMENSIONAL SCAN DATA, APPARATUS GENERATING PROSTHESIS FROM THREE DIMENSIONAL SCAN DATA AND COMPUTER READABLE MEDIUM HAVING PROGRAM FOR PERFORMING THE METHOD

(71) Applicant: IMAGOWORKS INC., Seoul (KR)

(72) Inventors: Eunhyeon Kim, Seoul (KR); Hannah Kim, Seoul (KR); Jinhyeok Choi, Seoul (KR); Dong Uk Kam, Seoul (KR); Taeseok Lee, Seongnam-si (KR); Bonjour Shin, Seoul (KR)

(73) Assignee: IMAGOWORKS INC., Seoul (KR)

( * ) Notice: Subject to any disclaimer, the term of this patent is extended or adjusted under 35 U.S.C. 154(b) by 186 days.

(21) Appl. No.: 18/527,263

(22) Filed: Dec. 2, 2023

(65) Prior Publication Data

US 2024/0193893 A1　　Jun. 13, 2024

(30) Foreign Application Priority Data

Dec. 7, 2022　(KR) ......................... 10-2022-0169727

(51) Int. Cl.
　　*G06T 19/20*　　　(2011.01)
　　*A61C 13/00*　　　(2006.01)
　　　　(Continued)

(52) U.S. Cl.
　　CPC .......... *G06T 19/20* (2013.01); *A61C 13/0004* (2013.01); *G06T 17/20* (2013.01);
　　　　(Continued)

(58) Field of Classification Search
　　CPC ..... G06T 19/20; G06T 17/20; G06T 2210/41; G06T 2219/2004; G06T 2219/2008;
　　　　(Continued)

(56) References Cited

U.S. PATENT DOCUMENTS

2006/0008776 A1* 1/2006 Orth .......................... A61C 5/77
　　　　　　　　　　　　　　　　　　433/215
2013/0204586 A1* 8/2013 Manzer ................... G06F 30/00
　　　　　　　　　　　　　　　　　　703/1
　　　　(Continued)

FOREIGN PATENT DOCUMENTS

EP　　　　2422740 B1 * 3/2013　............... A61C 5/77
EP　　　　3593754 B1 * 11/2023　......... A61C 13/0004
　　　　(Continued)

OTHER PUBLICATIONS

Wang, Jüttler, Zheng, Liu—Computation of Rotation Minimizing Frames—2008. (Year: 2008).*
　　　　(Continued)

*Primary Examiner* — Daniel F Hajnik
*Assistant Examiner* — Adeel Bash
(74) *Attorney, Agent, or Firm* — LEEPI

(57) ABSTRACT

An automated method for generating a prosthesis from a three dimensional ("3D") scan data, the method includes generating an intermediate surface of the prosthesis extending toward an outside of a prepared tooth from a margin line of the prepared tooth in the 3D scan data, generating an inner surface of the prosthesis by determining a gap from a surface of the prepared tooth, generating an outer surface of the prosthesis and connecting the outer surface of the prosthesis and the intermediate surface of the prosthesis.

21 Claims, 12 Drawing Sheets

(51) Int. Cl.
    *G06T 17/20*       (2006.01)
    *G16H 10/60*     (2018.01)

(52) U.S. Cl.
    CPC ......... *G16H 10/60* (2018.01); *G06T 2210/41* (2013.01); *G06T 2219/2004* (2013.01); *G06T 2219/2008* (2013.01); *G06T 2219/2016* (2013.01); *G06T 2219/2021* (2013.01)

(58) Field of Classification Search
    CPC ..... G06T 2219/2016; G06T 2219/2021; A61C 13/0004; G16H 10/60
    See application file for complete search history.

(56) References Cited

U.S. PATENT DOCUMENTS

| | | | | |
|---|---|---|---|---|
| 2013/0226534 A1* | 8/2013 | Fisker | .................... | B33Y 80/00 |
| | | | | 703/1 |
| 2018/0028294 A1* | 2/2018 | Azernikov | ........ | G06F 18/24143 |
| 2021/0059796 A1 | 3/2021 | Weiss et al. | | |

FOREIGN PATENT DOCUMENTS

| | | |
|---|---|---|
| JP | 2020508777 A | 3/2020 |
| KR | 20100127491 A | 12/2010 |
| KR | 20100128101 A | 12/2010 |
| KR | 20190057873 A | 5/2019 |
| KR | 20190071952 A | 6/2019 |
| KR | 102292872 B1 | 8/2021 |
| KR | 20210146154 A | 12/2021 |
| KR | 20220005250 A | 1/2022 |
| KR | 20220109065 A | 8/2022 |

OTHER PUBLICATIONS

Exocad GmbH—Designing the inside of the crown—Oct. 2022 (Year: 2022).*
3Shape—Incise (NPL)—2015 (Year: 2015).*
Kim et al.—Offsetting the polygonal model with nonmanifold features—2004 (Year: 2004).*
Yu et al.—Effect of different tooth preparation designs on the marginal and internal fit discrepancies of cobalt-chromium crowns produced by CAD and SLM processes—2021. (Year: 2021).*
International Search Report issued on Aug. 28, 2023.
Office action of the Japanese patent application issued on Jul. 2, 2024.
Dentbird Crown Tutorial | Crown Design (Aug. 2022), YouTube [online] [video], Augst 4, 2022 <URL:https://www.youtube.com/watch?v=LHsGupM3kAg>.

* cited by examiner

RECEIVING 3D SCAN DATA AND USER PARAMTER — S100

GENERATING INTERMEDIATE SURFACE — S200

GENERATING INNER SURFACE — S300

GENERATING OUTER SURFACE — S400

CONNECTING OUTER SURFACE AND INTERMEDIATE SURFACE — S500

ADJUSTING MINIMAL THICKNESS AND COMPENSATING CONTACT AREA — S600

OFFSET DIRECTION VECTOR

FIRST DIRECTION VECTOR($V_1$)

SECOND DIRECTION VECTOR($V_2 = I \times V_1$)

INSERTION DIRECTION VECTOR($I$)

NORMAL VECTOR OF PREP MESH TRIANGLE INCLUDING MARGIN LINE POINT

Margin line

Prep mesh

Margin line point

GENERATING PREP AREA BASED ON MARGIN LINE ──S310

REMOVING UNDERCUT AREA ──S320

DETERMINING NO CEMENT GAP, CEMENT GAP AND ADDITIONAL CEMENT GAP ──S330

APPLYING NO CEMENT GAP, CEMENT GAP AND ADDITIONAL CEMENT GAP TO SURFACE OF PREP AREA ──S340

BEFORE

AFTER

MINIMAL THICKNESS MODEL

INNER SURFACE

OUTER SURFACE

PREP

GINGIVA

PREP   CROWN

TARGET ARCH

ANTAGONIST ARCH

GINGIVA

CONTACT AREA

AUTOMATED METHOD FOR GENERATING PROSTHESIS FROM THREE DIMENSIONAL SCAN DATA, APPARATUS GENERATING PROSTHESIS FROM THREE DIMENSIONAL SCAN DATA AND COMPUTER READABLE MEDIUM HAVING PROGRAM FOR PERFORMING THE METHOD

PRIORITY STATEMENT

This application claims priority under 35 U.S.C. § 119 to Korean Patent Application No. 10-2022-0169727, filed on Dec. 7, 2022 in the Korean Intellectual Property Office (KIPO) and International Patent Application No. PCT/KR2022/021351 filed on Dec. 27, 2022, the contents of which are herein incorporated by reference in their entireties.

BACKGROUND

1. Technical Field

Embodiments relate to an automated method for generating a prosthesis from a three dimensional ("3D") scan data, an apparatus generating the prosthesis from the 3D scan data and a non-transitory computer-readable storage medium having stored thereon program instructions of the automated method for generating the prosthesis. More particularly, embodiments relate to an automated method for generating a prosthesis from a 3D scan data by generating an intermediate surface of the prosthesis, generating an inner surface of the prosthesis, generating an outer surface of the prosthesis and connecting the intermediate surface of the prosthesis and the outer surface of the prosthesis, an apparatus generating the prosthesis from the 3D scan data and a non-transitory computer-readable storage medium having stored thereon program instructions of the automated method for generating the prosthesis.

2. Description of the Related Art

A three dimensional ("3D") oral scan data refers to a scanned data of teeth and oral cavity by a 3D scanner, or a scanned data of an impression object or a reconstructed object of the teeth and the oral cavity by the 3D scanner. In prosthetic treatment such as in-ray, on-ray, and crown, dental treatment such as implant and orthodontic treatment, oral data of the patient may be acquired and be used to design prosthesis or implant, and to manufacture braces.

Conventionally, a method of generating a prosthesis manually after taking a direct model of the teeth and the oral cavity using alginate or the like has been mainly used. In order to make an anatomically correct prosthesis, a dentist or a dental technician may determine a degree of wear on adjacent teeth, a tooth number and occlusion information of an opposite tooth, and then generate the prosthesis. In the conventional prosthesis generating method, an operator may manually modify a general tooth shape according to the oral condition of each patient in consideration of the above information.

Conventionally, the prosthesis may be generated manually, work fatigue of the dentist or the dental technician may increase and accuracy and productivity of the prosthesis may decrease. In addition, the quality of the prosthesis and the time for generating the prosthesis may vary greatly depending on the proficiency of the operator.

SUMMARY

Embodiments provide an automated method for generating a prosthesis from a three dimensional ("3D") scan data by generating an intermediate surface of the prosthesis, generating an inner surface of the prosthesis, generating an outer surface of the prosthesis and connecting the intermediate surface of the prosthesis and the outer surface of the prosthesis.

Embodiments provide an apparatus generating a prosthesis from a 3D scan data.

Embodiments provide a non-transitory computer-readable storage medium having stored thereon program instructions of the automated method for generating a prosthesis from a 3D scan data.

In an example automated method for generating a prosthesis from a 3D scan data according to the present inventive concept, the method includes generating an intermediate surface of the prosthesis extending toward an outside of a prepared tooth from a margin line of the prepared tooth in the 3D scan data, generating an inner surface of the prosthesis by determining a gap from a surface of the prepared tooth, generating an outer surface of the prosthesis and connecting the outer surface of the prosthesis and the intermediate surface of the prosthesis.

In an embodiment, the intermediate surface may be determined by a predetermined width of the intermediate surface and an intermediate surface direction vector extending from the margin line.

In an embodiment, the intermediate surface may be determined based on the margin line, an insertion direction of the prosthesis, the width of the intermediate surface and an angle condition.

In an embodiment, the intermediate surface direction vector may be determined by rotating a first direction vector with respect to a second direction vector according to the angle condition. The second direction vector may be a cross product of an insertion direction vector representing the insertion direction and the first direction vector.

In an embodiment, the first direction vector of a margin line point in the margin line may be a normal vector of a mesh of the 3D scan data including the margin line point.

In an embodiment, the margin line may include a $(k-1)$-th margin line point, a k-th margin line point and a $(k+1)$-th margin line point which are adjacent to each other. When the $(k-1)$-th margin line point is $P_{k-1}$, the $(k+1)$-th margin line point is $P_{k+1}$, the first direction vector of the k-th margin line point is $V_1$ and the insertion direction vector is I, $V=P_{k+1}-P_{k-1}$ and $V_1=I \times V$ may be satisfied.

In an embodiment, the generating the intermediate surface may include obtaining a slave vector, a tangent vector and a reference vector using a rotation minimizing frames method at a margin line point in the margin line. The first direction vector of the margin line point may be determined as the reference vector of the margin line point.

In an embodiment, when the insertion direction is I, a number of surfaces of a prepared mesh data of the prepared tooth is N, normal vectors of surfaces of the prepared mesh data are $(n_1, \ldots n_N)$, $X_{opt}$ is a direction in which a normal vector of a point of the prepared mesh data is not obscured and T is a transpose function which switches row and column indices of a matrix, $I=\text{argmin}_{x_{opt} \in R^3} \Sigma_{i=1}^{N}(1-x_{opt}{}^T n_i)$ arguing may be satisfied.

In an embodiment, the generating the inner surface of the prosthesis may include determining a no cement gap having no gap between the inner surface of the prosthesis and a surface of the prepared tooth, determining a cement gap having a first gap between the inner surface of the prosthesis and the surface of the prepared tooth and determining an additional cement gap having an additional distance from the cement gap.

In an embodiment, the no cement gap and the cement gap may be determined based on a geodesic distance from a plane formed by the margin line.

In an embodiment, the additional cement gap may be determined based on a geodesic distance from a plane formed by the margin line and a curvature value of the prepared tooth.

In an embodiment, as the curvature value increases, an area of the additional cement gap may increase.

In an embodiment, the generating the inner surface of the prosthesis may further include removing a portion where a distance from a plane formed by the margin line is negative from a prepared mesh data corresponding to the prepared tooth.

In an embodiment, the generating the inner surface of the prosthesis may further include converting an area, in which the prepared tooth does not exist among areas located inside two outermost straight lines among parallel straight lines when the straight lines parallel to an insertion direction of the prosthesis are drawn to meet the prepared tooth, to an area in which the prepared tooth exists.

In an embodiment, the generating the outer surface of the prosthesis may include disposing a tooth library model corresponding to the prepared tooth at a position of the prepared tooth and deforming the tooth library model into a pre op data representing a pre-preparation state of the prepared tooth.

In an embodiment, the generating the outer surface of the prosthesis may include disposing a tooth library model corresponding to the prepared tooth at a position of the prepared tooth and deforming the tooth library model into a prosthesis outer surface data obtained by an artificial intelligence neural network.

In an embodiment, the automated method may further include modifying the outer surface such that a distance from the inner surface to the outer surface is a minimal thickness when the distance from the inner surface to the outer surface is less than the minimal thickness.

In an embodiment, the automated method may further include modifying the outer surface using a first distance between the prepared tooth and an adjacent tooth and a second distance between the prepared tooth and an opposite tooth.

In an embodiment, the connecting the outer surface of the prosthesis and the intermediate surface of the prosthesis may include displacing coordinates of a lower portion of the outer surface which does not correspond to the intermediate surface to coordinates of the intermediate surface.

In an example automated method for generating a prosthesis from a 3D scan data according to the present inventive concept, the method includes determining a tooth number of a prepared tooth from the 3D scan data using a first artificial intelligence neural network, determining a margin line of the prepared tooth using a second artificial intelligence neural network, generating an intermediate surface of the prosthesis extending toward an outside of the prepared tooth from the margin line of the prepared tooth, generating an inner surface of the prosthesis by determining a gap from a surface of the prepared tooth, generating an outer surface of the prosthesis using a third artificial intelligence neural network and connecting the outer surface of the prosthesis and the intermediate surface of the prosthesis.

In an example apparatus generating a prosthesis from a 3D scan data according to the present inventive concept, the apparatus is configured to generate an intermediate surface of the prosthesis extending toward an outside of a prepared tooth from a margin line of the prepared tooth in the 3D scan data, generate an inner surface of the prosthesis by determining a gap from a surface of the prepared tooth, generate an outer surface of the prosthesis and connect the outer surface of the prosthesis and the intermediate surface of the prosthesis.

In an example non-transitory computer-readable storage medium having stored thereon program instructions, the program instructions is executable by at least one hardware processor to generate an intermediate surface of a prosthesis extending toward an outside of a prepared tooth in a 3D scan data from a margin line of the prepared tooth in the 3D scan data, generate an inner surface of the prosthesis by determining a gap from a surface of the prepared tooth, generate an outer surface of the prosthesis and connect the outer surface of the prosthesis and the intermediate surface of the prosthesis.

According to the automated method and apparatus for generating the prosthesis from the 3D scan data, the prosthesis may be automatically generated by generating the intermediate surface of the prosthesis, generating the inner surface of the prosthesis, generating the outer surface of the prosthesis and connecting the intermediate surface of the prosthesis and the outer surface of the prosthesis.

In conventional dental CAD software, there may be significant differences in a time to generate the prosthesis and a quality of the prosthesis depending on the user's proficiency. In the method of manually generating the prosthesis by considering the opposite teeth and the adjacent teeth, there may be significant differences in results depending on the user's proficiency. According to the present inventive concept, when the 3D scan data and user parameters are input, the prosthesis is automatically generated from the 3D scan data so that even a user who is not skilled in generating prosthesis may generate a high quality prosthesis in a short time.

BRIEF DESCRIPTION OF THE DRAWINGS

The above and other features and advantages of the present inventive concept will become more apparent by describing in detailed embodiments thereof with reference to the accompanying drawings, in which.

DETAILED DESCRIPTION OF THE EMBODIMENTS

Figure 1:
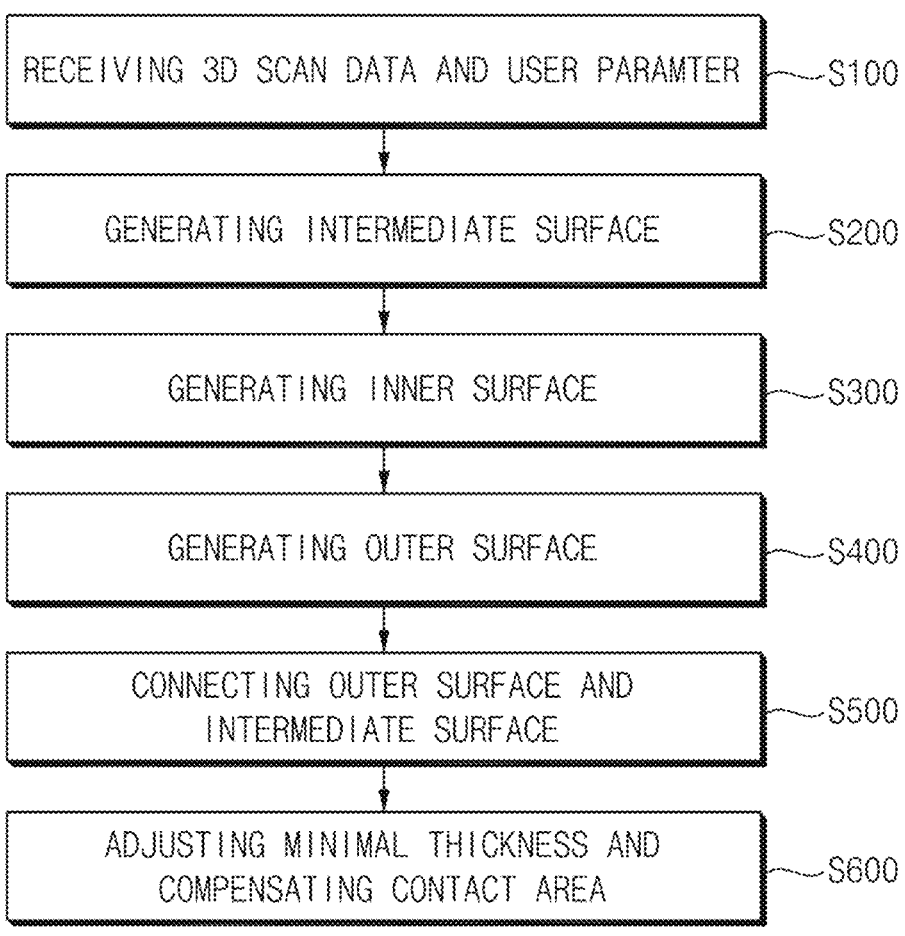
FIG. 1 is a flowchart diagram illustrating an automated method for generating a prosthesis from a three dimensional ("3D") scan data according to an embodiment of the present inventive concept.

The present inventive concept now will be described more fully hereinafter with reference to the accompanying drawings, in which embodiments of the present invention are shown. The present inventive concept may, however, be embodied in many different forms and should not be construed as limited to the embodiments set forth herein.

Rather, these embodiments are provided so that this disclosure will be thorough and complete, and will fully convey the scope of the present invention to those skilled in the art. Like reference numerals refer to like elements throughout.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the inventive concept as used herein.

Hereinafter, the present inventive concept will be explained in detail with reference to the accompanying drawings.

FIG. 1 is a flowchart diagram illustrating an automated method for generating a prosthesis from a three dimensional ("3D") scan data according to an embodiment of the present inventive concept.

Referring to FIG. 1, the automated method for generating the prosthesis from the 3D scan data according to an embodiment of the present inventive concept includes an operation S200 of generating an intermediate surface of the prosthesis, an operation S300 of generating an inner surface of the prosthesis by determining a gap from a surface of the prepared tooth, an operation S400 of generating an outer surface of the prosthesis and an operation S500 of connecting the outer surface of the prosthesis and the intermediate surface of the prosthesis. The intermediate surface of the prosthesis extends toward an outside of a prepared tooth from a margin line of the prepared tooth in the 3D scan data.

The apparatus for automatically generating the prosthesis from the 3D scan data according to an embodiment of the present inventive concept generates the intermediate surface of the prosthesis, the inner surface of the prosthesis by determining the gap from the surface of the prepared tooth and the outer surface of the prosthesis and connects the outer surface of the prosthesis and the intermediate surface of the prosthesis.

The automated method for generating the prosthesis from the 3D scan data may further include an operation S100 receiving the 3D scan data and a user parameter.

The automated method for generating the prosthesis from the 3D scan data may further include an operation (S600, ADJUSTING MINIMAL THICKNESS) of modifying the outer surface such that a distance from the inner surface to the outer surface is a minimal thickness when the distance from the inner surface to the outer surface is less than the minimal thickness.

The automated method for generating the prosthesis from the 3D scan data may further include an operation (S600, COMPENSATION CONTACT AREA) of modifying the outer surface using a first distance between the prepared tooth and an adjacent tooth and a second distance between the prepared tooth and an opposite tooth.

Herein, the 3D scan data refers to a scanned data of teeth and oral cavity by a 3D scanner, or a scanned data of an impression object or a reconstructed object of the teeth and the oral cavity by the 3D scanner. For example, the 3D scan data may be a mesh data including 3D vertices and triangles or quadrangles generated by connecting the vertices. A file extension of the 3D scan data may not be limited. For example, the file extension of the 3D scan data may be one of ply, obj and stl.

Herein, the prepared tooth may mean a tooth prepared for a crown. The prepared tooth may mean a tooth obtained by cutting a part of the tooth. To generate a single crown, an operation of shaving off a natural tooth to make it easier to place a prosthesis is needed. The natural tooth which is shaved off may be referred to the prepared tooth. The margin line may refer to an edge portion of the prepared tooth. The margin line may represent a boundary between the prepared tooth and a gum.

A preprocessing may be needed for the 3D scan data. For example, a registration between a maxilla scan data and a mandible scan data may be operated. In addition, a registration of the maxilla scan data, the mandible scan data and a bite scan data may be operated.

For example, when a pre op scan data including a pre-preparation state of the prepared tooth exists, the pre op scan data may also be registered to the 3D scan data including the prepared tooth.

To automatically generate the prosthesis from the 3D scan data, several basic data may be needed. The basic data may include a tooth number of a target tooth, a margin line of the target tooth, an insertion direction of the prosthesis, adjacent tooth information of the target tooth, occlusal surface information of the target tooth, opposite tooth information of the target tooth, etc. The basic data may be automatically determined using an artificial intelligence. Alternatively, the basic data may be determined in a program. The basic data determined using the artificial intelligence or determined in the program may be modified by the user.

The insertion direction of the prosthesis may represent a direction in which a prosthesis model is inserted into the prepared tooth. The insertion direction of the prosthesis may be determined using normal vectors of surfaces of a prepared mesh data of the prepared tooth.

For example, when the insertion direction is I, a number of the surfaces of the prepared mesh data is N, the normal vectors are $(n_1, \ldots n_N)$, $X_{opt}$ is a direction in which a normal vector of a point of the prepared mesh data is not obscured and T is a transpose function which switches row and column indices of a matrix, $I = \mathrm{argmin}_{x_{opt} \in R^3} \Sigma_{i=1}^{N} (1 - x_{opt}^{\tau} n_i)$ may be satisfied.

Expressing in a formula that the normal vector n is not obscured in direction x, $xTn > 0$. $xTn > 0$ may mean that an angle between x and n is an acute angle. When the angle between x and n is an acute angle, $xTn > 0$. When the angle between x and n is a right angle, $xTn = 0$. When the angle between x and n is an obtuse angle, $xTn < 0$. Therefore, $X_{opt}$ may be a direction in which an average value of the angle with the normal vectors on the all surfaces of the prepared mesh data is lowest.

The automated method for generating the prosthesis from the 3D scan data according to an embodiment of the present inventive concept may include an operation of determining a tooth number of the prepared tooth from the 3D scan data using a first artificial intelligence neural network, an operation of determining the margin line of the prepared tooth using a second artificial intelligence neural network, an operation of generating the intermediate surface of the prosthesis, an operation of generating the inner surface of the prosthesis by determining the gap from the surface of the prepared tooth, an operation of generating the outer surface of the prosthesis using a third artificial intelligence neural network and an operation of connecting the outer surface of the prosthesis and the intermediate surface of the prosthesis. In the present embodiment, the tooth number of the prepared tooth is automatically determined using the first artificial intelligence neural network, the margin line of the prepared tooth is automatically determined using the second artificial intelligence neural network and the outer surface of the prepared tooth is automatically determined using the third artificial intelligence neural network.

The automated method for generating the prosthesis from the 3D scan data of the present inventive concept may be operated by a computing apparatus.

Figure 2:
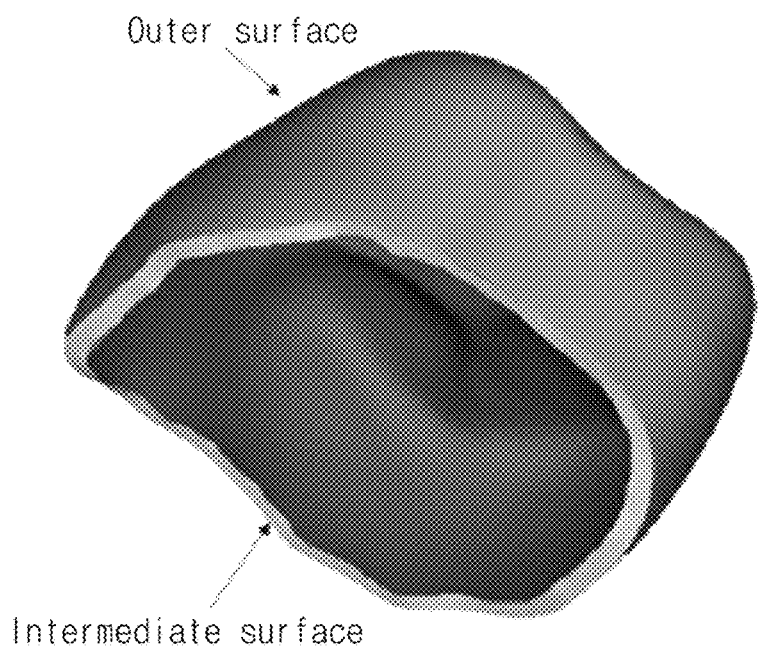
FIG. 2 is a drawing illustrating an outer surface of the prosthesis and an intermediate surface of the prosthesis.
Figure 3:
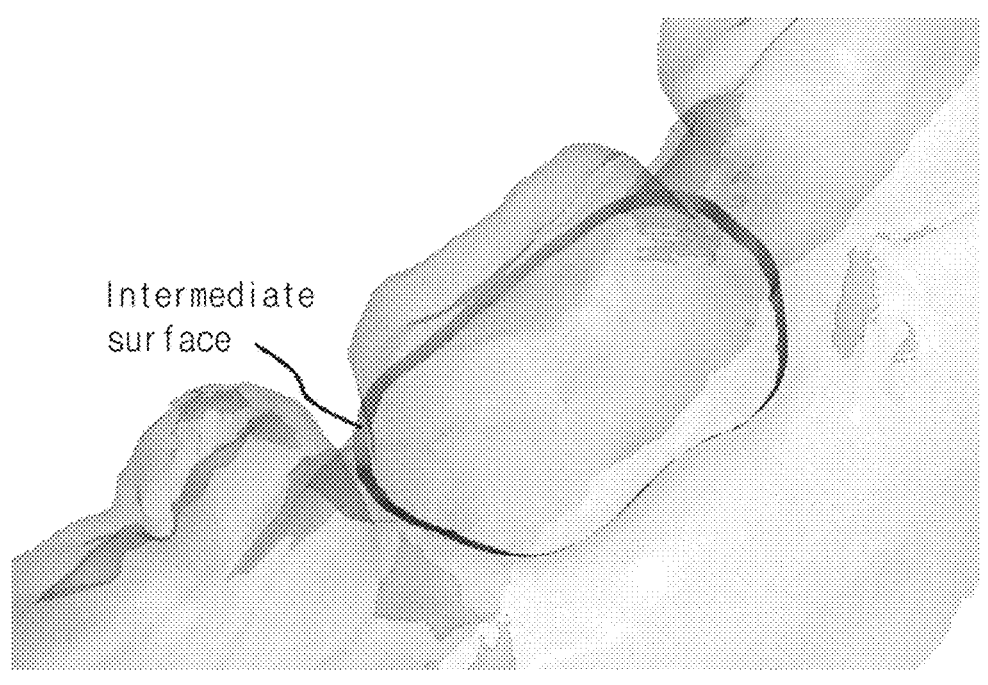
FIG. 3 is a drawing illustrating a prepared tooth and the intermediate surface of the prosthesis corresponding to the prepared tooth.

FIG. 2 is a drawing illustrating an outer surface of the prosthesis and the intermediate surface of the prosthesis. FIG. 3 is a drawing illustrating the prepared tooth and the intermediate surface of the prosthesis corresponding to the prepared tooth.

Referring to FIGS. 1 to 3, the intermediate surface may be an extending portion of the prosthesis extending toward the outside of the prepared tooth from the margin line of the prepared tooth in the 3D scan data. The intermediate surface may mean a surface connecting the outer surface and the inner surface. For example, the intermediate surface may be closest to a patient's gum among the surfaces of the prosthesis.

For example, the intermediate surface may be determined by a predetermined width of the intermediate surface and an intermediate surface direction vector extending from the margin line. The intermediate surface may be determined based on the margin line, the insertion direction of the prosthesis, the width of the intermediate surface and an angle condition.

Herein, the width of the intermediate surface may be a user parameter appropriately adjusted by the user. In addition, the angle condition may also be a user parameter. Alternatively, the width of the intermediate surface and the angle condition may be predetermined values.

For example, the angle condition may represent an angle at which the intermediate surface of the prosthesis is extended such that the intermediate surface of the prosthesis does not pierce the patient's gum.

Figure 4:
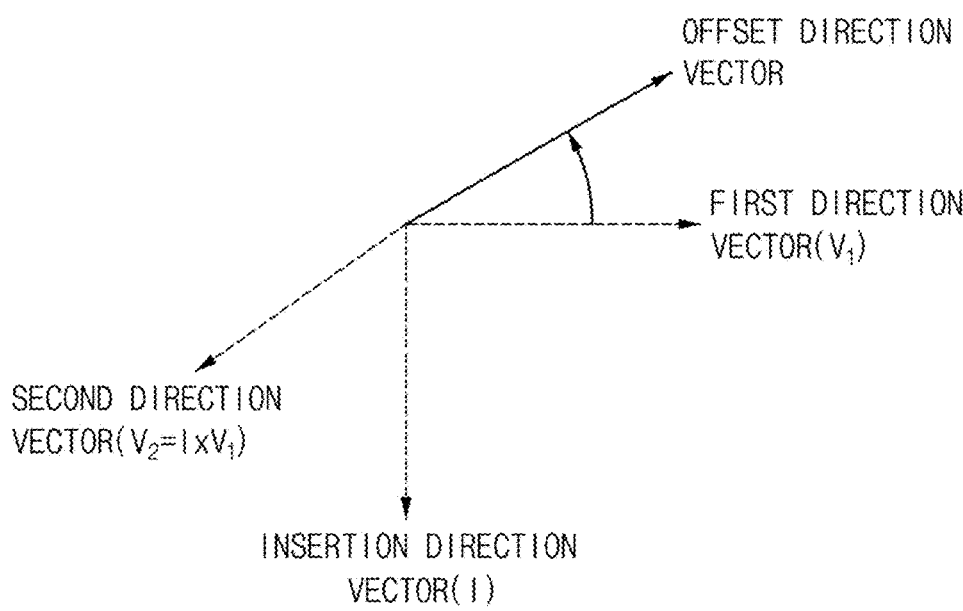
FIG. 4 is a drawing illustrating an intermediate surface direction vector used in an operation of generating the intermediate surface of FIG. 1.

FIG. 4 is a drawing illustrating the intermediate surface direction vector used in the operation S200 of generating the intermediate surface of FIG. 1.

Referring to FIGS. 1 to 4, the intermediate surface direction vector may be determined by rotating a first direction vector $V_1$ with respect to a second direction vector $V_2$ according to the angle condition (Bottom angle of FIG. 4).

The second direction vector $V_2$ may be a cross product of an insertion direction vector I representing the insertion direction and the first direction vector $V_1$ ($V_2 = I \times V_1$).

Herein, the first direction vector $V_1$ may refer to a vector generally parallel to a plane formed by the margin line. The first direction vector $V_1$ may be obtained through various methods.

Figure 5:
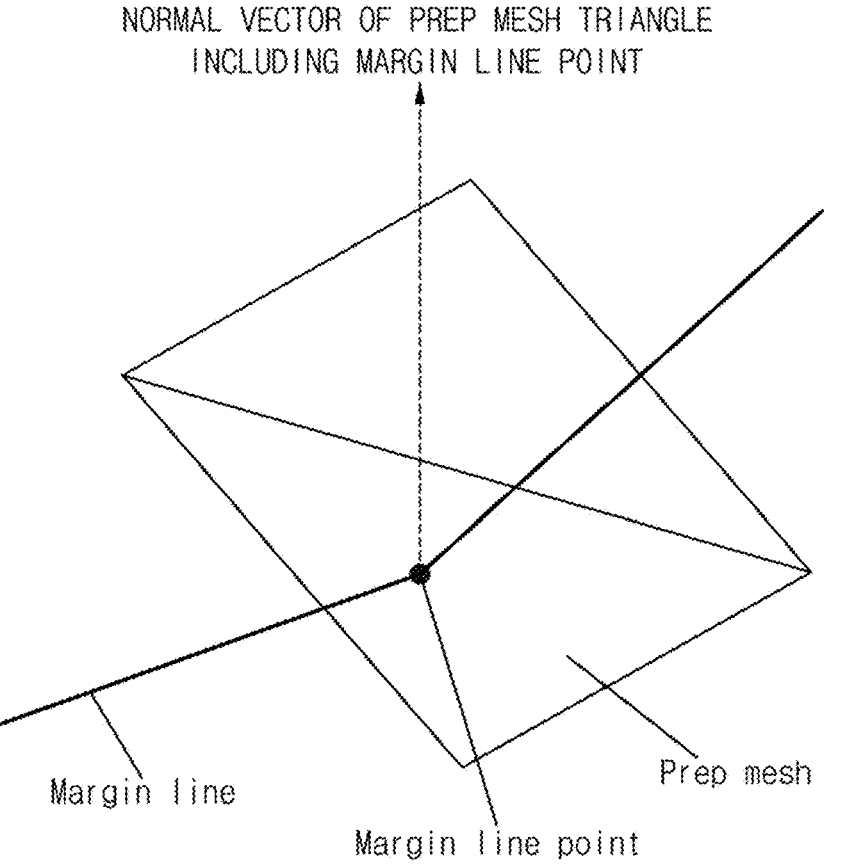
FIG. 5 is a drawing illustrating an example of a method of generating a first direction vector used in the operation of generating the intermediate surface of FIG. 1.

FIG. 5 is a drawing illustrating an example of a method of generating the first direction vector $V_1$ used in the operation S200 of generating the intermediate surface of FIG. 1.

Referring to FIGS. 1 to 5, the first direction vector of a margin line point in the margin line may be a normal vector of a mesh (Prep mesh) of the 3D scan data including the margin line point.

Figure 6:
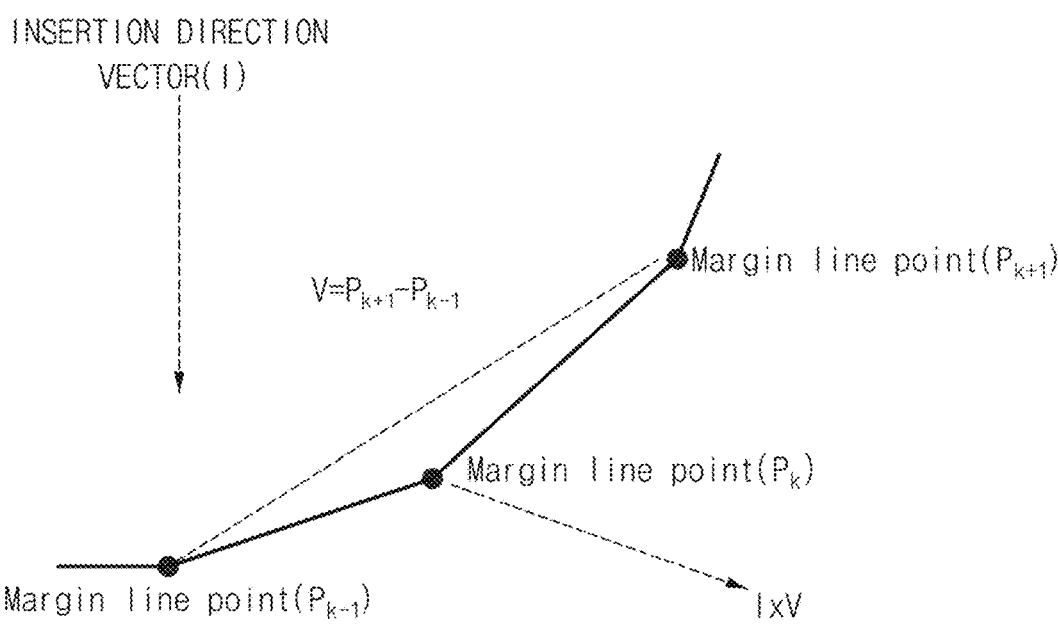
FIG. 6 is a drawing illustrating an example of a method of generating the first direction vector used in the operation of generating the intermediate surface of FIG. 1.

FIG. 6 is a drawing illustrating an example of a method of generating the first direction vector $V_1$ used in the operation S200 of generating the intermediate surface of FIG. 1.

Referring to FIGS. 1 to 4 and 6, the margin line may include a (k−1)-th margin line point $P_{k-1}$, a k-th margin line point $P_k$ and a (k+1)-th margin line point $P_{k+1}$ which are adjacent to each other. When the (k−1)-th margin line point is $P_{k-1}$, the (k+1)-th margin line point is $P_{k+1}$, the first direction vector of the k-th margin line point $P_k$ is $V_1$ and the insertion direction vector is I, $V=P_{k+1}-P_{k-1}$ and $V_1=I \times V$ may be satisfied.

Figure 7:
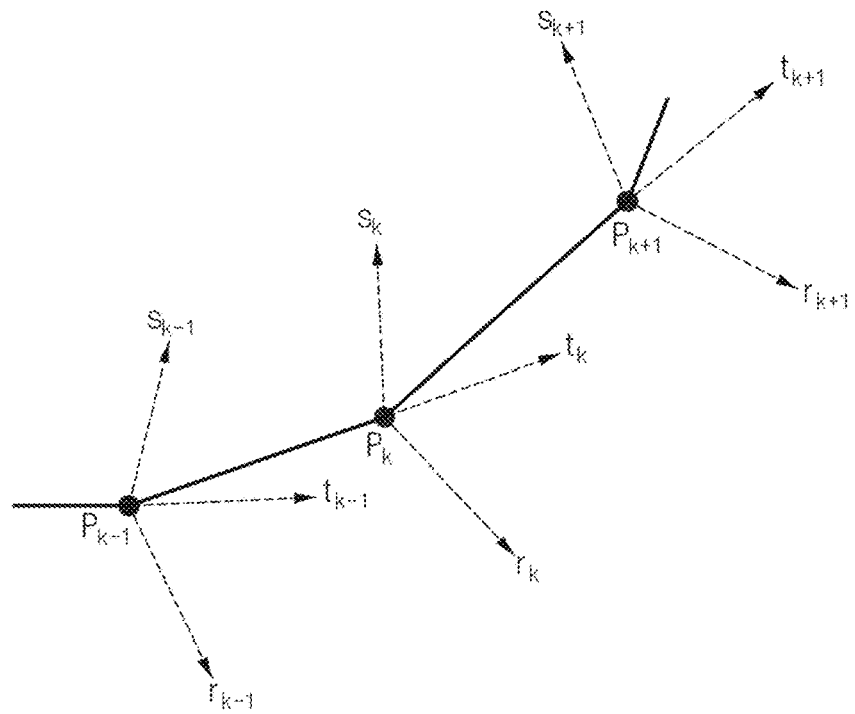
FIG. 7 is a drawing illustrating an example of a method of generating the first direction vector used in the operation of generating the intermediate surface of FIG. 1.

FIG. 7 is a drawing illustrating an example of a method of generating the first direction vector $V_1$ used in the operation S200 of generating the intermediate surface of FIG. 1.

Referring to FIGS. 1 to 4 and 7, the operation S200 of generating the intermediate surface may include an operation of obtaining a slave vector s, a tangent vector t and a reference vector r using a rotation minimizing frames method at a margin line point in the margin line. The first direction vector $V_1$ of the margin line point may be determined as the reference vector r of the margin line point.

The margin line may include a (k−1)-th margin line point $P_{k-1}$, a k-th margin line point $P_k$ and a (k+1)-th margin line point $P_{k+1}$ which are adjacent to each other. The first direction vector of the (k−1)-th margin line point $P_{k-1}$ may be $r_{k-1}$ of FIG. 7. The first direction vector of the k-th margin line point $P_k$ may be $r_k$ of FIG. 7. The first direction vector of the (k+1)-th margin line point $P_{k+1}$ may be $r_{k+1}$ of FIG. 7.

Figure 8:
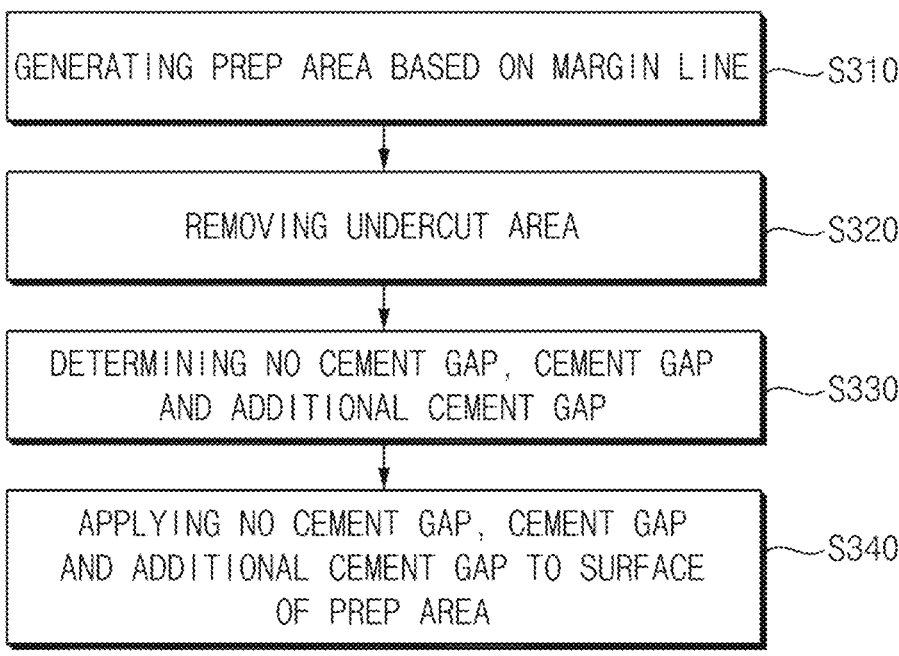
FIG. 8 is a flowchart diagram illustrating an operation of generating an inner surface of FIG. 1.
Figure 9:
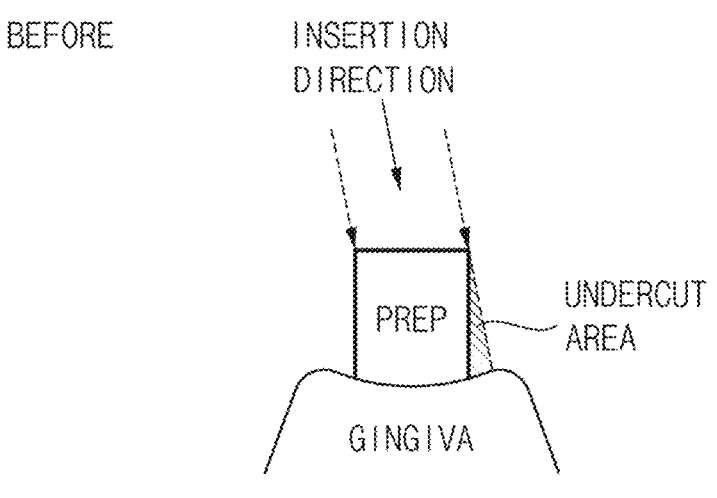
FIG. 9 is a drawing illustrating an operation of removing an undercut area of FIG. 8.
Figure 9:
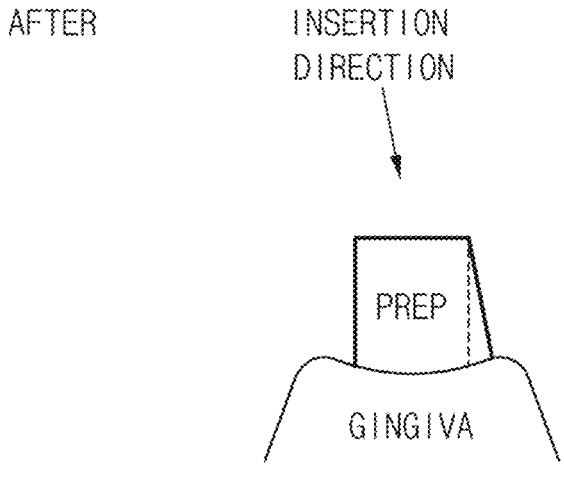
Figure 10:
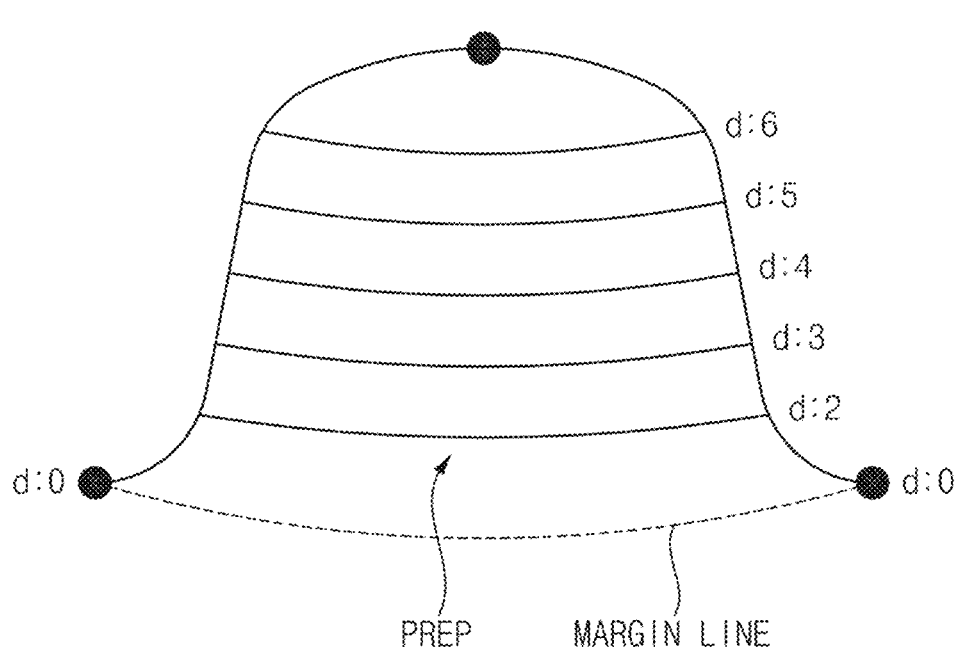
FIG. 10 is a drawing illustrating a geodesic distance used in an operation of determining a no cement gap, a cement gap and an additional cement gap in FIG. 8.
Figure 11:
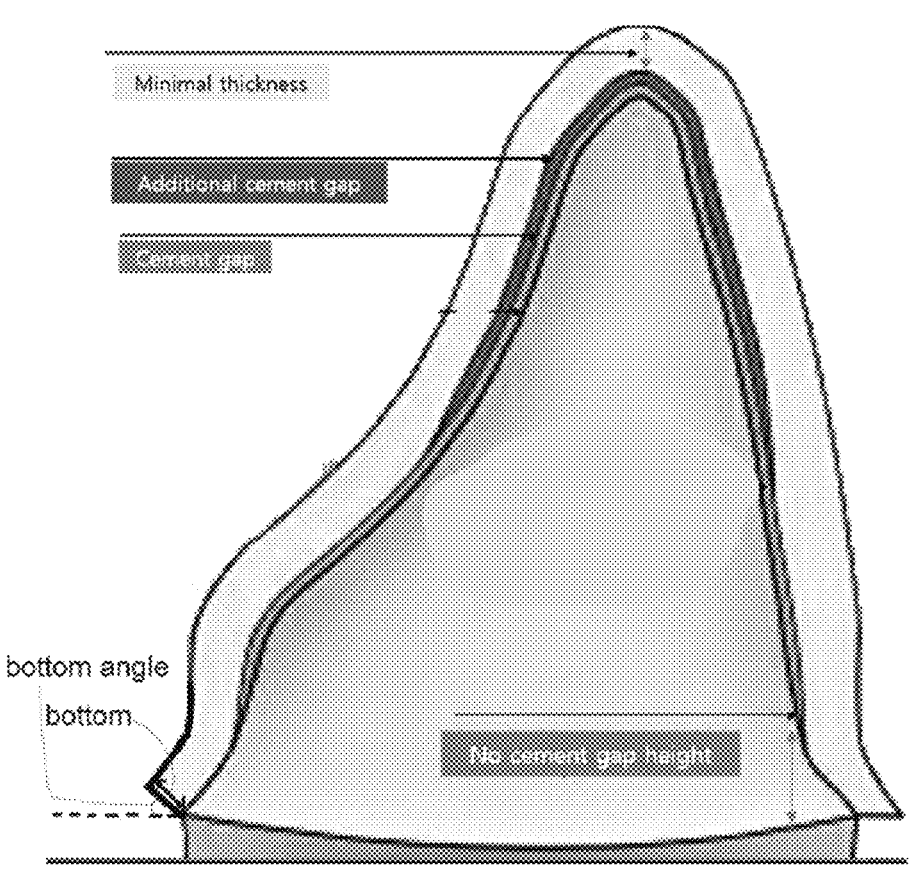
FIG. 11 is a drawing illustrating the no cement gap, the cement gap and the additional cement gap of FIG. 10.

FIG. 8 is a flowchart diagram illustrating the operation S300 of generating the inner surface of FIG. 1. FIG. 9 is a drawing illustrating an operation S320 of removing an undercut area of FIG. 8. FIG. 10 is a drawing illustrating a geodesic distance used in an operation S330 of determining a no cement gap, a cement gap and an additional cement gap in FIG. 8. FIG. 11 is a drawing illustrating the no cement gap, the cement gap and the additional cement gap of FIG. 10.

Referring to FIGS. 1 to 11, the operation S300 of generating the inner surface of the prosthesis may include an operation S310 of generating a prep area based on a margin line, an operation S320 of removing an undercut area, an operation S330 of determining the no cement gap, the cement gap and the additional cement gap and an operation S340 of applying the no cement gap, the cement gap and the additional cement gap to a surface of the prep area to generate the inner surface of the prosthesis.

For example, in the operation S310 of generating the prep area based on the margin line, a portion where the distance from the plane formed by the margin line is negative may be removed from the prepared mesh data corresponding to the prepared tooth.

For example, in the operation S320 of removing the undercut area, an area, in which the prepared tooth does not exist among areas located inside two outermost straight lines among parallel straight lines when the straight lines parallel to the insertion direction of the prosthesis are drawn to meet the prepared tooth, may be converted to an area in which the prepared tooth exists.

An area indicated as the undercut area in an upper portion of FIG. 9 is the area in which the prepared tooth does not exist among the areas located inside the two outermost straight lines among the parallel straight lines. The area indicated as the undercut area in an upper portion of FIG. 9 may be converted to the area in which the prepared tooth exists as shown in a lower portion of FIG. 9.

The no cement gap may mean an area where the inner surface of the prosthesis has no gap with the surface of the prepared tooth. In FIG. 11, in an area corresponding to a no cement gap height or less, the inner surface of the prosthesis may have a no cement gap. Due to the no cement gap, an adhesive filled in the cement gap and the additional cement gap does not flow out.

The cement gap may mean an area where the inner surface of the prosthesis has a first gap with the surface of the prepared tooth. The cement gap may be filled with the adhesive so that the prepared tooth and the prosthesis may be adhered.

The no cement gap and the cement gap may be determined based on a geodesic distance from the plane formed by the margin line. The geodesic distance from the plane formed by the margin line is illustrated in FIG. 10.

For example, an area where the geodesic distance is less than a threshold distance among the prep areas may be determined as the no cement gap. For example, an area where the geodesic distance is equal to or greater than the threshold distance among the prep areas may be determined as the cement gap.

The additional cement gap may refer to an area having an additional distance from the cement gap. The additional cement gap may be filled with the adhesive so that the prepared tooth and the prosthesis may be adhered. The additional cement gap may be set in a portion where it is predicted that the prepared tooth and the prosthesis may not be sufficiently adhered only by the cement gap.

For example, the additional cement gap may be determined based on the geodesic distance from the plane formed by the margin line and a curvature value of the prepared tooth.

As the curvature value increases, an area of the additional cement gap may increase. An area having a great curvature value may be an area where the adhesive is relatively likely to flow. Accordingly, the adhesion between the prepared tooth and the prosthesis may be increased by adding the additional cement gap.

For example, an area where the geodesic distance is equal to or greater than the threshold distance and where the curvature value of the prepared tooth is equal to or greater than a threshold curvature value among the prep areas may be determined as the additional cement gap.

"bottom" in FIG. 11 may mean the width of the intermediate surface and "bottom angle" in FIG. 11 may mean the intermediate surface direction vector determined by the angle condition.

Figure 12:
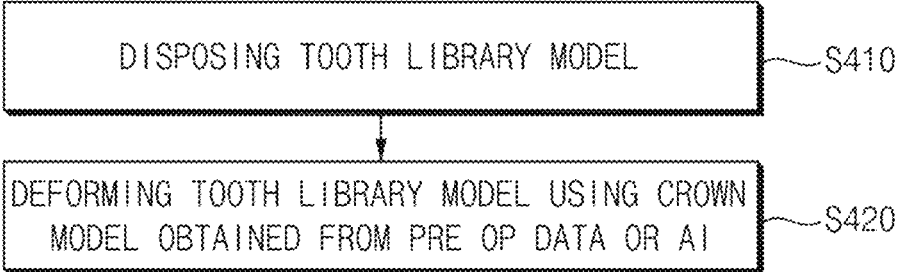
FIG. 12 is a flowchart diagram illustrating an operation of generating the outer surface of FIG. 1.

FIG. 12 is a flowchart diagram illustrating an operation S400 of generating the outer surface of FIG. 1.

Referring to FIGS. 1 to 12, for example, the operation S400 of generating the outer surface may include an operation S410 of disposing a tooth library model corresponding to the prepared tooth at a position of the prepared tooth and an operation S420 of deforming the tooth library model into the pre op data representing the pre-preparation state of the prepared tooth.

Alternatively, the operation S400 of generating the outer surface may include an operation S410 of disposing a tooth library model corresponding to the prepared tooth at a position of the prepared tooth and an operation S420 of deforming the tooth library model into a prosthesis outer surface data obtained by an artificial intelligence neural network. The dental library model is a kind of sample tooth (a standard tooth) used to manufacture the prostheses, the implants and the braces and may have a typical tooth shape.

The dental library model may have one sample tooth (the standard tooth) for each tooth number. The 3D oral scan data are captured by the 3D scanner so that the 3D oral scan data may have a low degree of completion of the mesh. When the degree of the completion of the mesh is low, a 3D printing may be inappropriate for manufacturing the prostheses, the implants and the braces. In contrast, the 3D dental library model may have a high degree of completion of the mesh. Thus, when the prostheses, the implants and the braces are manufactured by deforming the 3D dental library model, the 3D printing may be very suitable for manufacturing the prostheses, the implants and the braces. Accordingly, when the 3D dental library model is aligned with the patient's oral scan data, the 3D dental library model aligned with the oral scan data may be an intermediate model suitable for digitally manufacturing prostheses, implants and braces.

In the operation S410 of disposing the tooth library model at the position of the prepared tooth, landmarks may be used. Landmarks of the 3D scan data and landmarks of the tooth library model are extracted and then the tooth library model may be disposed on the 3D scan data such that the landmarks of the 3D scan data and the landmarks of the tooth library model match.

Figure 13:
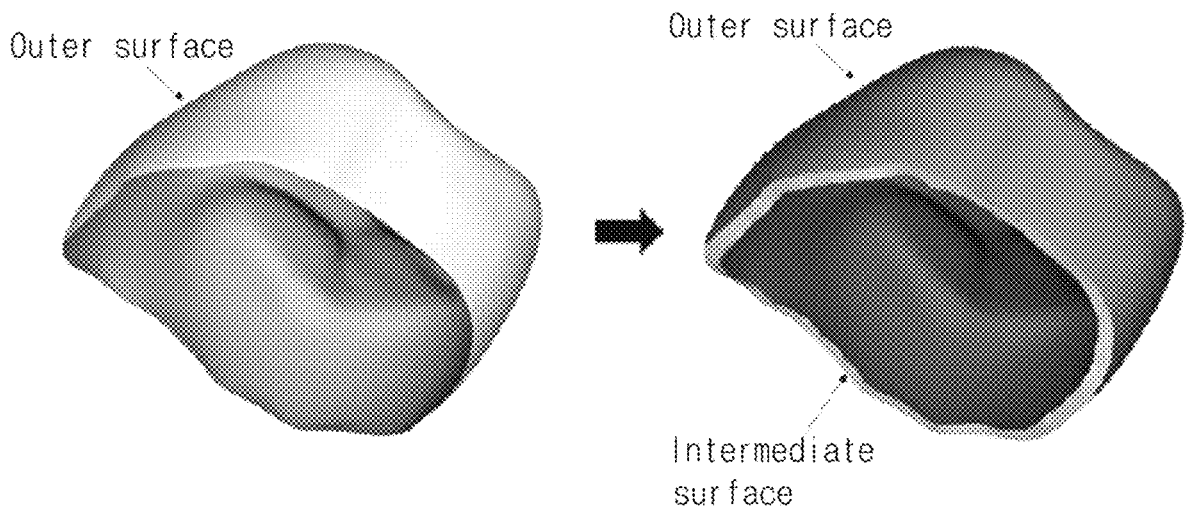
FIG. 13 is a drawing illustrating an operation of connecting the outer surface and the intermediate surface of FIG. 1.

FIG. 13 is a drawing illustrating an operation S500 of connecting the outer surface and the intermediate surface of FIG. 1.

Referring to FIGS. 1 to 13, coordinates of a lower portion of the outer surface which does not correspond to the intermediate surface may be displaced to coordinates of the intermediate surface in the operation S500 of connecting the outer surface and the intermediate surface.

For example, a pair of an outer surface model (a deformed library model) of the prosthesis generated at a position of the target tooth and an outermost line of the intermediate surface may be determined and the outer surface model may be transformed such that the outer surface model matches the outermost line of the intermediate surface.

Figure 14:
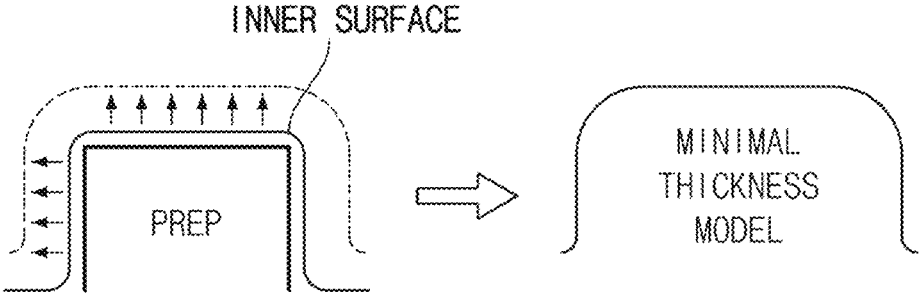
FIG. 14 is a drawing illustrating a minimal thickness used in an operation of adjusting the minimal thickness of FIG. 1.
Figure 15:
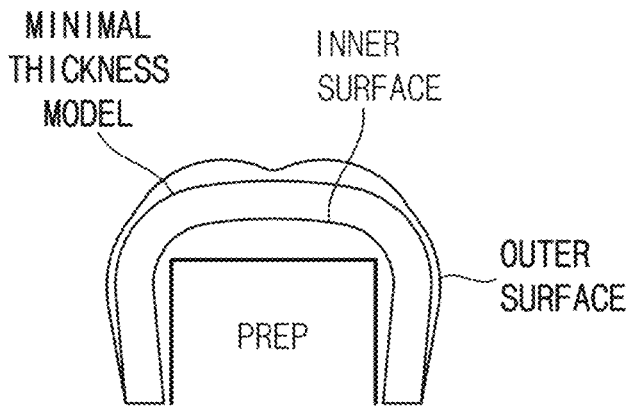
FIG. 15 is a drawing illustrating the operation of adjusting the minimal thickness of FIG. 1.
Figure 16:
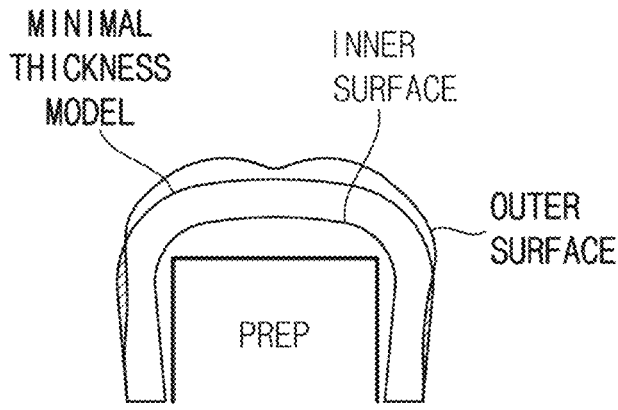
FIG. 16 is a drawing illustrating the operation of adjusting the minimal thickness of FIG. 1.

FIG. 14 is a drawing illustrating a minimal thickness used in an operation S600 of adjusting the minimal thickness of FIG. 1. FIG. 15 is a drawing illustrating the operation S600 of adjusting the minimal thickness of FIG. 1. FIG. 16 is a drawing illustrating the operation S600 of adjusting the minimal thickness of FIG. 1.

Referring to FIGS. 1 to 16, the automated method for generating the prosthesis from the 3D scan data may further include the operation (S600, ADJUSTING MINIMAL THICKNESS) of modifying the outer surface such that the distance from the inner surface to the outer surface is the minimal thickness when the distance from the inner surface to the outer surface is less than the minimal thickness.

As shown in a left portion of FIG. 14, the minimum thickness may be defined from the inner surface of the prosthesis. The minimum thickness may refer to a thickness value required to stably produce the prosthesis by a 3D printing method or a milling method. A right portion of FIG. 14 represents a minimal thickness model generated by extending the inner surface of the prosthesis by the minimum thickness.

The outer surface of the prosthesis may be modified such that the outer surface of the prosthesis is located outside an outer surface of the minimal thickness model.

In FIG. 15, the outer surface of the prosthesis is located entirely outside the outer surface of the minimal thickness model, so that the outer surface of the prosthesis may not be modified.

In contrast, in FIG. 16, a part of the outer surface of the prosthesis is located inside the outer surface of the minimal thickness model so that the outer surface of the prosthesis located inside the outer surface of the minimal thickness model may be modified to match the outer surface of the minimal thickness model.

Figure 17:
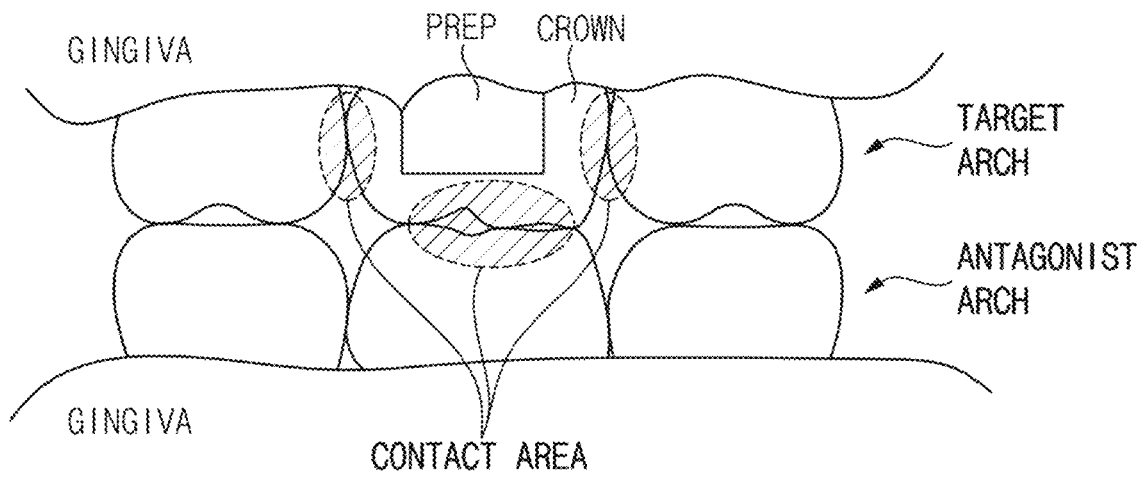
FIG. 17 is a drawing illustrating the operation of compensating a contact area of FIG. 1.

FIG. 17 is a drawing illustrating the operation of compensating a contact area of FIG. 1.

Referring to FIGS. 1 to 17, the automated method for generating the prosthesis from the 3D scan data may further include an operation (S600, COMPENSATION CONTACT AREA) of modifying the outer surface using the first distance between the prepared tooth and the adjacent tooth and the second distance between the prepared tooth and the opposite tooth.

Herein the first distance between the prepared tooth and the adjacent tooth and the second distance between the prepared tooth and the opposite tooth may be user parameters inputted by the user.

According to the present embodiment, the prosthesis may be automatically generated by generating the intermediate surface of the prosthesis, generating the inner surface of the prosthesis, generating the outer surface of the prosthesis and connecting the intermediate surface of the prosthesis and the outer surface of the prosthesis.

In conventional dental CAD software, there may be significant differences in a time to generate the prosthesis and a quality of the prosthesis depending on the user's proficiency. In the method of manually generating the prosthesis by considering the opposite teeth and the adjacent teeth, there may be significant differences in results depending on the user's proficiency. According to the present inventive concept, when the 3D scan data and user parameters are input, the prosthesis is automatically generated from the 3D scan data so that even a user who is not skilled in generating prosthesis may generate a high quality prosthesis in a short time.

According to an embodiment of the present inventive concept, a non-transitory computer-readable storage medium having stored thereon program instructions of the automated method for generating the prosthesis from the 3D scan data may be provided. The above mentioned method may be written as a program executed on the computer. The method may be implemented in a general purpose digital computer which operates the program using a computer-readable medium. In addition, the structure of the data used in the above mentioned method may be written on a computer readable medium through various means. The computer readable medium may include program instructions, data files and data structures alone or in combination. The program instructions written on the medium may be specially designed and configured for the present inventive concept, or may be generally known to a person skilled in the computer software field. For example, the computer readable medium may include a magnetic medium such as a hard disk, a floppy disk and a magnetic tape, an optical recording medium such as CD-ROM and DVD, a magneto-optical medium such as floptic disc and a hardware device specially configured to store and execute the program instructions such as ROM, RAM and a flash memory. For example, the program instructions may include a machine language codes produced by a compiler and high-level language codes which may be executed by a computer using an interpreter or the like. The hardware device may be configured to operate as one or more software modules to perform the operations of the present inventive concept.

In addition, the above mentioned automated method for generating the prosthesis from the 3D scan data may be implemented in a form of a computer-executed computer program or an application which are stored in a storage method.

The present inventive concept is related to the automated method for generating the prosthesis from the 3D scan data, the apparatus for automatically generating the prosthesis from the 3D scan data and the non-transitory computer-readable storage medium having stored thereon program instructions of the automated method for generating the prosthesis from the 3D scan data. According to the present inventive concept, the time and the effort for generating the prosthesis may be reduced and the accuracy and the productivity of the prosthesis may be enhanced.

The foregoing is illustrative of the present inventive concept and is not to be construed as limiting thereof. Although a few embodiments of the present inventive concept have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims. The present inventive concept is defined by the following claims, with equivalents of the claims to be included therein.

What is claimed is:

1. An automated method for generating a prosthesis from a three dimensional ("3D") scan data, the method comprising:

generating an intermediate surface of the prosthesis extending toward an outside of a prepared tooth from a margin line of the prepared tooth in the 3D scan data;

generating an inner surface of the prosthesis by determining a gap from a surface of the prepared tooth;

generating an outer surface of the prosthesis; and connecting the outer surface of the prosthesis and the intermediate surface of the prosthesis, wherein an intermediate surface direction vector is determined by rotating a first direction vector with respect to a second direction vector according to the angle condition, and wherein the first direction vector of a margin line point in the margin line is a normal vector of a mesh of the 3D scan data including the margin line point.

2. The automated method of claim 1, wherein the intermediate surface is determined by a predetermined width of the intermediate surface and the intermediate surface direction vector extending from the margin line.

3. The automated method of claim 2, wherein the intermediate surface is determined based on the margin line, an insertion direction of the prosthesis, the width of the intermediate surface and an angle condition.

4. The automated method of claim 3, wherein the second direction vector is a cross product of an insertion direction vector representing the insertion direction and the first direction vector.

5. The automated method of claim 4, wherein the margin line includes a (k−1)-th margin line point, a k-th margin line point and a (k+1)-th margin line point which are adjacent to each other, and wherein when the (k−1)-th margin line point is $P_{k-1}$, the (k+1)-th margin line point is $P_{k+1}$, the first direction vector of the k-th margin line point is $V_1$ and the insertion direction vector is I, $V=P_{k+1}-P_{k-1}$ and $V_1=I \times V$ are satisfied.

6. The automated method of claim 4, wherein the generating the intermediate surface comprises obtaining a slave vector, a tangent vector and a reference vector using a rotation minimizing frames method at a margin line point in the margin line, and wherein the first direction vector of the margin line point is determined as the reference vector of the margin line point.

7. The automated method of claim 3, wherein when the insertion direction is I, a number of surfaces of a prepared mesh data of the prepared tooth is N, normal vectors of surfaces of the prepared mesh data are $\{n_1, \ldots, n_N\}$, $x_{opt}$ is a direction in which a normal vector of a point of the prepared mesh data is not obscured and T is a transpose function which switches row and column indices of a matrix, $I=\text{argmin}_{x_{opt} \in R^3} \Sigma_{i=1}^{N}(1-x_{opt}^{\tau} n_i)$ is satisfied.

8. The automated method of claim 1, wherein the generating the inner surface of the prosthesis comprises:

determining a no cement gap having no gap between the inner surface of the prosthesis and a surface of the prepared tooth;

determining a cement gap having a first gap between the inner surface of the prosthesis and the surface of the prepared tooth; and determining an additional cement gap having an additional distance from the cement gap.

9. The automated method of claim 8, wherein the no cement gap and the cement gap are determined based on a geodesic distance from a plane formed by the margin line.

10. The automated method of claim 8, wherein the additional cement gap is determined based on a geodesic distance from a plane formed by the margin line and a curvature value of the prepared tooth.

11. The automated method of claim 10, wherein as the curvature value increases, an area of the additional cement gap increases.

12. The automated method of claim 8, wherein the generating the inner surface of the prosthesis further comprises:

removing a portion where a distance from a plane formed by the margin line is negative from a prepared mesh data corresponding to the prepared tooth.

13. The automated method of claim 8, wherein the generating the inner surface of the prosthesis further comprises:

converting an area, in which the prepared tooth does not exist among areas located inside two outermost straight lines among parallel straight lines when the straight lines parallel to an insertion direction of the prosthesis are drawn to meet the prepared tooth, to an area in which the prepared tooth exists.

14. The automated method of claim 1, wherein the generating the outer surface of the prosthesis comprises:

disposing a tooth library model corresponding to the prepared tooth at a position of the prepared tooth; and deforming the tooth library model into a pre op data representing a pre-preparation state of the prepared tooth.

15. The automated method of claim 1, wherein the generating the outer surface of the prosthesis comprises:

disposing a tooth library model corresponding to the prepared tooth at a position of the prepared tooth; and deforming the tooth library model into a prosthesis outer surface data obtained by an artificial intelligence neural network.

16. The automated method of claim 1, further comprising:

modifying the outer surface such that a distance from the inner surface to the outer surface is a minimal thickness when the distance from the inner surface to the outer surface is less than the minimal thickness.

17. The automated method of claim 1, further comprising:
modifying the outer surface using a first distance between the prepared tooth and an adjacent tooth and a second distance between the prepared tooth and an opposite tooth.

18. The automated method of claim 1, wherein the connecting the outer surface of the prosthesis and the intermediate surface of the prosthesis comprises:
displacing coordinates of a lower portion of the outer surface which does not correspond to the intermediate surface to coordinates of the intermediate surface.

19. An automated method for generating a prosthesis from a three dimensional ("3D") scan data, the method comprising:
determining a tooth number of a prepared tooth from the 3D scan data using a first artificial intelligence neural network;
determining a margin line of the prepared tooth using a second artificial intelligence neural network;
generating an intermediate surface of the prosthesis extending toward an outside of the prepared tooth from the margin line of the prepared tooth;
generating an inner surface of the prosthesis by determining a gap from a surface of the prepared tooth;
generating an outer surface of the prosthesis using a third artificial intelligence neural network; and
connecting the outer surface of the prosthesis and the intermediate surface of the prosthesis,
wherein an intermediate surface direction vector is determined by rotating a first direction vector with respect to a second direction vector according to the angle condition, and
wherein the first direction vector of a margin line point in the margin line is a normal vector of a mesh of the 3D scan data including the margin line point.

20. An apparatus for automatically generating a prosthesis from a three dimensional ("3D") scan data, the apparatus configured to:

generate an intermediate surface of the prosthesis extending toward an outside of a prepared tooth from a margin line of the prepared tooth in the 3D scan data;
generate an inner surface of the prosthesis by determining a gap from a surface of the prepared tooth;
generate an outer surface of the prosthesis; and
connect the outer surface of the prosthesis and the intermediate surface of the prosthesis,
wherein an intermediate surface direction vector is determined by rotating a first direction vector with respect to a second direction vector according to the angle condition, and
wherein the first direction vector of a margin line point in the margin line is a normal vector of a mesh of the 3D scan data including the margin line point.

21. A non-transitory computer-readable storage medium having stored thereon program instructions, the program instructions executable by at least one hardware processor to:
generate an intermediate surface of a prosthesis extending toward an outside of a prepared tooth in a three dimensional ("3D") scan data from a margin line of the prepared tooth in the 3D scan data;
generate an inner surface of the prosthesis by determining a gap from a surface of the prepared tooth;
generate an outer surface of the prosthesis; and
connect the outer surface of the prosthesis and the intermediate surface of the prosthesis,
wherein an intermediate surface direction vector is determined by rotating a first direction vector with respect to a second direction vector according to the angle condition, and
wherein the first direction vector of a margin line point in the margin line is a normal vector of a mesh of the 3D scan data including the margin line point.

* * * * *